United States Patent [19]

Muderlak et al.

[11] Patent Number: 4,968,456
[45] Date of Patent: Nov. 6, 1990

[54] ELECTRICAL AIR FRESHENER FOR AUTOMOBILES

[75] Inventors: Kenneth Muderlak, Milwaukee, Wis.; Charles Toler, Chicago; Ira Taylor, Hinsdale, both of Ill.

[73] Assignee: Turbo Blast Air Freshener Co., Inc., Chicago, Ill.

[21] Appl. No.: 361,038

[22] Filed: Jun. 2, 1989

[51] Int. Cl.$^5$ ................................................ B01F 3/04
[52] U.S. Cl. ........................... 261/030; 261/DIG. 65; 422/124; 137/60
[58] Field of Search .................... 261/30, DIG. 65; 422/124; 137/60

[56] References Cited

U.S. PATENT DOCUMENTS

| | | |
|---|---|---|
| D. 269,116 | 5/1983 | Armbruster . |
| 2,349,402 | 5/1944 | Beibin .................... 239/60 |
| 2,614,820 | 10/1952 | Boydjieff . |
| 2,629,149 | 2/1953 | Yaffe . |
| 2,737,572 | 3/1956 | Ernst . |
| 2,784,465 | 3/1957 | Strobel-Fuchs . |
| 3,006,042 | 10/1961 | Calandra . |
| 3,538,866 | 11/1970 | Gaines . |
| 3,722,182 | 3/1973 | Gilbertson . |
| 3,930,797 | 1/1976 | Gertz . |
| 3,941,034 | 3/1976 | Helwig et al. . |
| 3,990,848 | 11/1976 | Corris . |
| 3,993,444 | 11/1976 | Brown . |
| 4,007,875 | 2/1977 | Stolz et al. . |
| 4,035,451 | 7/1977 | Tringali . |
| 4,040,568 | 8/1977 | Mason, Jr. et al. .............. 239/60 |
| 4,059,422 | 11/1977 | Steiner ........................ 55/418 |
| 4,065,261 | 12/1977 | Fukada . |
| 4,067,692 | 1/1978 | Farris . |
| 4,078,891 | 3/1978 | Madjar . |
| 4,102,656 | 7/1978 | Koritz . |
| 4,197,271 | 4/1980 | Fenstermaker et al. . |
| 4,200,229 | 4/1980 | Spector . |
| 4,208,012 | 6/1980 | Dutcher ..................... 239/60 |
| 4,223,598 | 9/1980 | Suzuki et al. . |
| 4,226,829 | 10/1980 | Mike . |
| 4,227,446 | 10/1980 | Sone et al. . |
| 4,245,550 | 1/1981 | Suzuki et al. . |
| 4,271,092 | 6/1981 | Sullivan et al. . |
| 4,274,843 | 5/1981 | Sone et al. . |
| 4,276,236 | 6/1981 | Sullivan et al. . |
| 4,301,095 | 11/1981 | Mettler et al. . |
| 4,309,382 | 1/1982 | Miller . |
| 4,339,079 | 7/1982 | Sato et al. . |
| 4,370,300 | 1/1983 | Mori et al. . |
| 4,377,399 | 3/1983 | Bryson . |
| 4,383,377 | 5/1983 | Crafton . |
| 4,432,938 | 2/1984 | Meetze, Jr. . |
| 4,518,404 | 5/1985 | Vaillant et al. . |
| 4,523,870 | 6/1985 | Spector . |
| 4,568,521 | 2/1986 | Spector . |
| 4,604,245 | 8/1986 | Gutierrez ...................... 261/30 |
| 4,666,638 | 5/1987 | Baker et al. . |
| 4,695,435 | 9/1987 | Spector . |
| 4,707,338 | 11/1987 | Spector . |
| 4,722,264 | 2/1988 | DeGuisseppe . |
| 4,743,406 | 5/1988 | Steiner et al. ................. 239/60 |

FOREIGN PATENT DOCUMENTS 2411011  8/1979  France ........................... 239/60

Primary Examiner—Tim Miles
Attorney, Agent, or Firm—Willian Brinks Olds Hofer Gilson & Lione

[57] ABSTRACT

An electrical air freshener designed to be plugged into an automobile cigarette lighter receptacle is disclosed. The air freshener includes a housing or body; an electrical motor within the housing connectable to a source of electrical current; a switch on the exterior of the housing for switching on and off the electrical current to the motor; air flow inlets at the back of the housing; odor emitting means mounted at the front of the housing; a fan connected to the motor and mounted within the housing such that operation of the motor creates air flow into the housing through the inlets, past the fan and motor and out through the odor emitting means. A stem protrudes from the back of the housing and is attached for insertion into the cigarette lighter receptacle. In the preferred embodiment the stem extends non-perpendicularly from the rear of the housing.

18 Claims, 2 Drawing Sheets

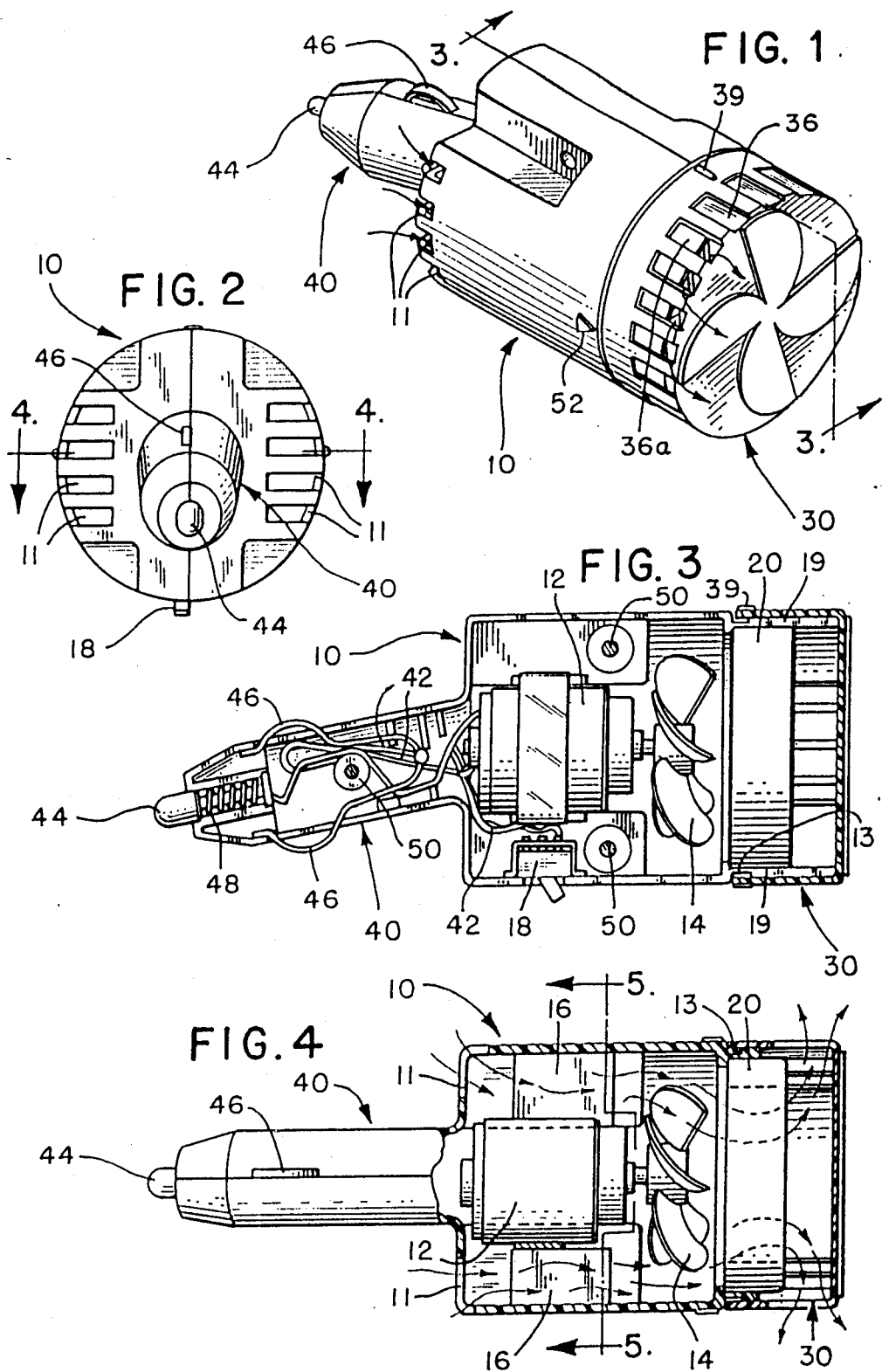

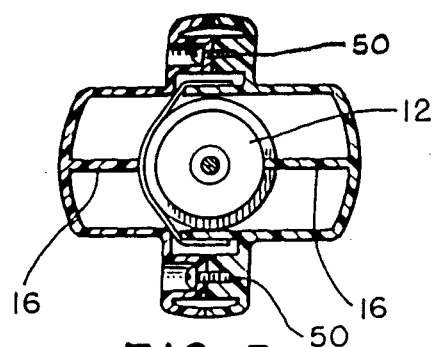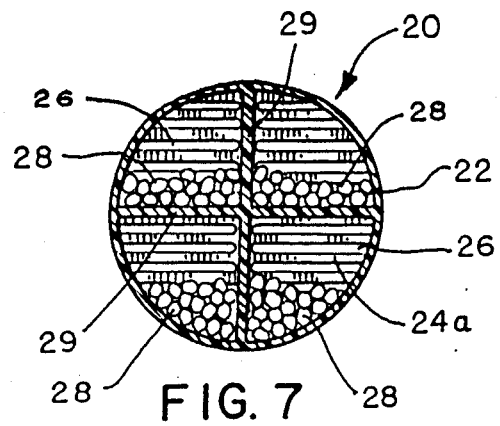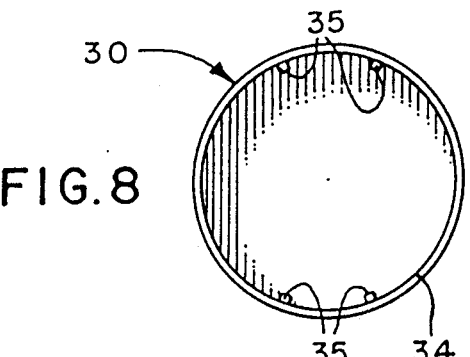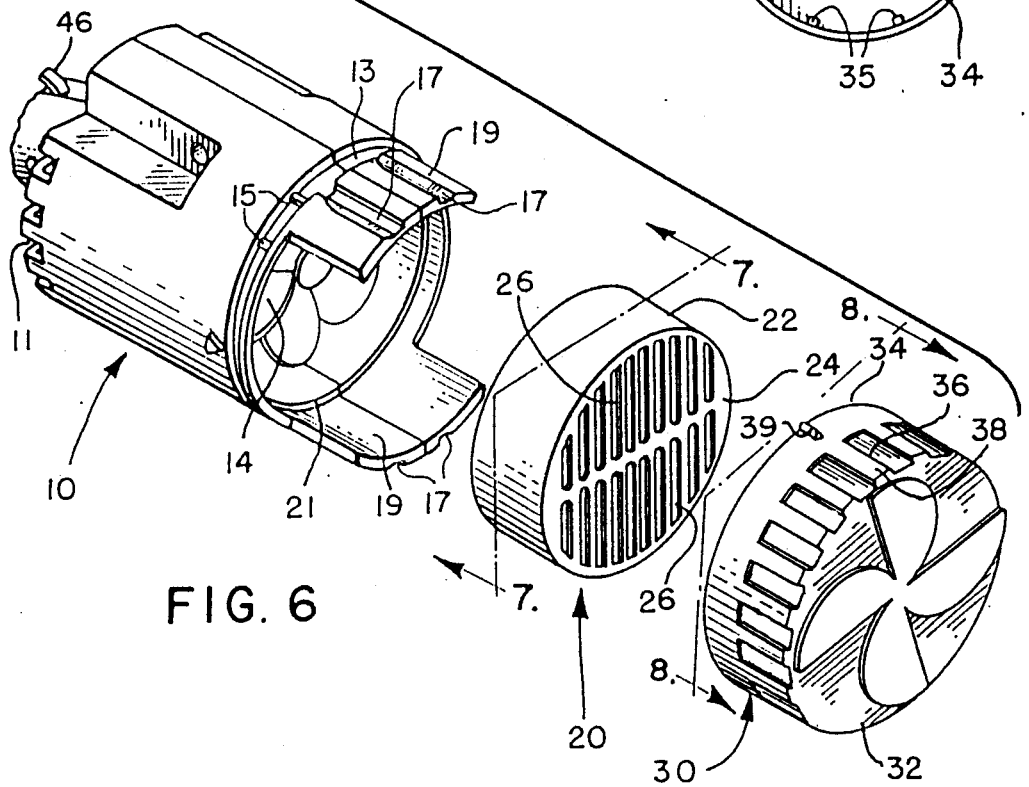

ELECTRICAL AIR FRESHENER FOR AUTOMOBILES

BACKGROUND OF THE INVENTION

The present invention relates to an electrical air freshener for automobiles and cartridge used in the air freshener. More particularly, the present invention relates to an air freshener that plugs into the cigarette lighter receptacle on the automobile dash-board and blows a stream of air past an odor emitting means.

One type of air freshener commonly used in automobiles generally comprises an article which is suspended in the passenger compartment having a solid or semi-solid fragrance emitting medium. The fragrance is circulated in the passenger compartment only by natural currents and diffusion. One problem with such a device is that its fragrance is emitted constantly, even when the automobile is not occupied Thus, in order to make the device long lasting, the relative rate of fragrance emission must be kept low.

Numerous devices have been patented for freshening, deodorizing and/or purifying the air in an automobile passenger compartment Examples of such patents include U.S. Pat. No. 3,006,042 to Calandra, U.S. Pat. No. 3,722,182 to Gilbertson and U.S. Pat. No. 4,604,245 to Gutierrez. None of these devices, however, has come to widespread use. Further, numerous patents have issued on devices which produce an air flow stream past a vaporizable product to condition the air in a closed space, such as a room. U.S. Pat. No. 3,993,444 to Brown, U.S. Pat. No. 4,271,092 to Sullivan et al., and U.S. Pat. No. 4,432,938 to Meltze, Jr. These devices have not been adapted for use in automobiles.

Applicants are aware of a device, referred to as the "Marquesa Jet", which they believe has been sold in foreign countries but not in the U.S. The Marquesa Jet includes a body or housing, a motor and a centrifugal type blower. Extending perpendicular from the rear of the body is a stem which fits into a cigarette lighter receptacle. On the end and extending from one side of the stem are electrical contacts which match up with the electrical system of the cigarette lighter receptacle. A switch on the outside of the body completes the electrical circuit between these contacts and the motor. In front of the blower is a cylindrical cartridge which holds fragrance beads and has open grid ends which allow air to pass through the cartridge. A cap over the end of the body can be turned to open and close air passageways downstream from the cartridge.

The Marquesa Jet has several problems which applicants' invention overcomes. First, the air intake for the Marquesa Jet is located near the front of the body, countercurrent to the airflow through the cartridge. Since the air intake is near the exit, air tends to recirculate through the device. Second, the centrifugal type blower does not create very good air flow through the device. Additionally, when the device is inserted into a cigarette lighter, the cartridge is turned on its side and the fragrance beads fall to one side of the cartridge. Hence most of the air flow through the cartridge goes over the top of the pile of beads.

SUMMARY OF THE INVENTION

The electrical air freshener of the present invention includes a housing or body; an electrical motor within the housing connectable to a source of electrical current; a switch on the exterior of the housing for switching on and off the electrical current to the motor; air flow inlets at the back of the housing; odor emitting means mounted at the front of the housing; a fan connected to the motor and mounted within the housing such that operation of the motor creates air flow into the housing from the inlets at the back, past the fan and motor and out through the odor emitting means; and a stem protruding from the back of the housing adapted for insertion in the cigarette lighter receptacle of an automobile dashboard. Having the air inlets in the rear of the housing and having a direct flow through the device provides good circulation of freshened air in the automobile compartment.

In the preferred embodiment of the invention, an axial-flow type fan is utilized. This provides for good flow rates. Also in the preferred embodiment, the stem extends from the back of the housing at an angle non-perpendicular to the back of the housing. This allows the device to be rotated to direct the flow of air in different directions and avoid interference with other objects mounted on or near the dashboard, which objects of course vary with each automobile.

In another aspect of the invention, the cartridge comprises an annular housing and two open-spaced grids attached to the opposite ends of the housing, enclosing a cylindrical volume Inside the housing are fragrance beads and at least one internal spacer which compartmentalizes the housing. This spacer divides the beads so that when the cartridge is turned on its side, all of the beads do not fall in one heap at the bottom of the cartridge. Preferably, two spacers spanning perpendicular diameters of the housing are utilized, which form four equal compartments, assuring at least half the fragrance beads will always be contained in the top half of the cartridge when the cartridge is held in a vertical position.

These and other advantages, as well as the invention itself, will best be understood in reference to the drawings and detailed description of the preferred embodiment.

BRIEF DESCRIPTION OF THE DRAWINGS

FIG. 1 is a perspective view of the preferred electrical air freshener of the present invention.

FIG. 2 is a rear elevational view of the air freshener of FIG. 1.

FIG. 3 is a sectional view taken along line 3—3 of FIG. 1.

FIG. 4 is a sectional view taken along line 4—4 of FIG. 2.

FIG. 5 is a sectional view taken along line 5—5 of FIG. 4.

FIG. 6 is an exploded perspective view of the electrical air freshener of FIG. 1.

FIG. 7 is a sectional view of the cartridge of the preferred embodiment taken along line 7—7 of FIG. 6.

FIG. 8 is a sectional view of the cap taken along line 8—8 of FIG. 6.

DETAILED DESCRIPTION OF THE DRAWINGS AND PREFERRED EMBODIMENT OF THE INVENTION

The preferred embodiment of the electrical air freshener for automobiles of the present invention is shown in FIG. 1, with an exploded view in FIG. 6. The air freshener device has several main components: a housing 10, a cartridge 20 and a cap 30. Extending in a non-perpendicular fashion from the rear of the housing 10 is stem 40. The housing 10 and stem 40 are assembled from two pieces of integrally molded plastic, held together by screws 50 (FIGS. 3 and 5). Formed in the rear of the housing are a plurality of air intake slots 11. The motor 12 is held in place by flanges 16 integrally molded with the housing 10 (best seen in FIG. 5). Mounted on the housing 10 so as to be accessible from outside the device is a switch 18.

As shown in FIG. 3, the stem 40 includes electrical contacts and wiring 42 for carrying electrical current between the automobile cigarette lighter receptacle and the motor 12. There are two types of electrical contacts, a rear contact 44 and two side contacts 46. The contacts are all spring mounted. A coil spring 48 is used to bias the rear contact 44. The side contacts 46 are made from one continuous piece of flat metal which is bent in a "U" shape. The rigidity of the metal provides a spring characteristic to the contacts 46 The contacts 46 are preferably mounted on opposite sides of the stem.

Extending from the front of the housing 10 are two semi-circular extensions 19, best seen in FIG. 6. The extensions are not as thick as the front wall of the housing 10. This provides a seating ring 21 against which the cartridge 20 fits when the device is assembled. The cartridge 20 fits snugly into the area between the extensions 19. The cap 30 fits snugly over the outside of the extensions 19.

The cartridge 20, best shown in FIGS. 6 and 7, is made of two pieces. It has an annular wall 22 integrally molded with one end piece 24. The other end piece 24a is removable and snaps into place in the inside end of the annular wall 22. Both end pieces 24 and 24a include numerous openings 26, making a grid-like structure through which air can pass.

Inside the cartridge 20 are numerous fragrance beads 28 (FIG. 7). Such beads are available from Elux Co. Ltd., Korea. Other aromatic material may be used as well. A set of spacers 29 are integrally molded with the annular wall 22 and end piece 24. In the preferred embodiment, the spacers 29 extend across perpendicular diameters of the cartridge, dividing the volume into four equal compartments. Thus, no matter which direction the cartridge is turned, a large number of pellets will be retained in the central area of the cartridge.

The cap 30 is an integrally molded plastic piece, and includes a solid front 32 and a ribbed side wall 34. The spacers 36 between the ribs 38 are solid except in two sections covering two opposing 90° arcs, in which the spacers 36a are open to air flow. When the cap 30 is placed over the end of the housing 10, the extensions 19 and the spacers 36 and 36a cooperate to either block the air flow passages (when the open spacers 36a overlap the extension 19) or provide air passage (when the solid spacers 36 overlap the extension 19) (see FIG. 1).

The cap is removeable, but is held in place by four bumps 35 molded on the inside wall at the rear of the cap (FIG. 8). When the cap is in place, the bumps 35 fit within a sliding groove 13 formed at the base of extension 19, best seen in FIG. 6. Stops 15 are formed at intervals around groove 13 to cooperate with bumps 35 so that the cap 20 rotates only 90° between an open and a closed position but no further. Guideways 17 are formed in extensions 19 to allow the bumps 35 to slide down into groove 13 when the cap 30 is placed over the cartridge 20 and extensions 19. At their bottoms, the guideways 17 are beveled so that the bumps 35 may not easily go back up, thus helping to hold the cap 30 onto the end of the housing 10. However, markings 52 and 39 are provided respectively on the housing 10 and cap 30 to indicate when the bump 35 and guideways 17 are in alignment to facilitate removal of the cap 30 for cartridge replacement.

It should be understood that the preferred embodiment described in detail herein is illustrative of various aspects of the invention and that various changes and modifications to the presently preferred embodiment may be made. Therefore, the following claims, including all equivalents, define the scope of the invention.

We claim:

1. An electrical air freshener for automobiles comprising:
   (a) a housing having a front and a back,
   (b) an electric motor within the housing, connectable to a source of electrical current,
   (c) a switch on the exterior of the housing for switching on and off the electrical current to the motor,
   (d) air flow inlets at the back of the housing,
   (e) odor emitting means mounted at the front of the housing,
   (f) a fan connected to the motor and mounted within the housing such that operation of the motor creates air flow into the housing from the inlets at the back of the housing, past the fan and motor and out through the odor emitting means; and
   (g) a stem protruding from the back of the housing adapted for insertion into the cigarette lighter receptacle on an automobile dashboard.

2. The electrical air freshener of claim 1 wherein the stem extends from the housing at an angle non-perpendicular to the back of the housing.

3. The electrical air freshener of claim 1 wherein the stem further includes electrical contacts positioned to make electrical circuit contact with electrical contacts of the automobile cigarette lighter receptacle and wherein the contacts on the stem include a plurality of spring mounted contacts biased to protrude from the side walls of the stem.

4. The electrical air freshener of claim 1 wherein the odor emitting means comprises a cartridge containing fragrance beads.

5. The electrical air freshening device of claim 4 wherein the cartridge includes at least one internal spacer sufficient to compartmentalize the pellets into a plurality of compartments within the cartridge.

6. The electrical air freshener of claim 4 wherein the cartridge has a cross sectional area of essentially the same size as the cross sectional area of the housing.

7. The electrical air freshener of claim 1 wherein the fan comprises a plurality of vanes radiating from a hub connected to the motor.

8. The electrical air freshener of claim 1 further comprising a cap adapted to fit over the front of the housing, said cap and housing having openings and blockages cooperating to form air flow passages which are opened and closed by rotation of the cap.

9. An electrical air freshener for automobiles comprising:
   (a) an electrically operated fan,
   (b) a structure for mounting the fan to the automobile, said mounting structure having a stem adapted for tight insertion into a cylindrical cigarette lighter receptacle of the automobile, the stem including electrical contacts for transferring electrical current between said receptacle and the electrically operated fan, the stem further being connected to the remainder of said mounting structure such that when said stem is inserted in said receptacle, the axis of rotation of the fan is non-colinear with the center line of said cylindrical receptacle, and (c) means for mounting an odor emitting means in the path of the air flow generated by said fan.

10. The electrical air freshener of claim 9 wherein the electrical contacts include a plurality of spring mounted contacts biased to protrude from the side walls of the stem.

11. The electrical air freshener of claim 9 further comprising a cartridge containing fragrance beads mounted in said means for mounting an odor emitting means, said cartridge including at least one internal spacer sufficient to compartmentalize the pellets into a plurality of compartments within the cartridge.

12. The electrical air freshener of claim 9 wherein the fan comprises a plurality of vanes radiating from a hub.

13. The electrical air freshener of claim 9 wherein the structure for mounting the fan comprises
(a) a housing having a front and back, said stem protruding from said back;
(b) air flow inlets at the back of the housing, and
(c) wherein said means for mounting an odor emitting means comprises a cartridge containing fragrance beads mounted at the front of the housing.

14. The electrical air freshener of claim 13 wherein the cartridge has a cross-sectional area of essentially the same size as the cross-sectional area of the housing.

15. The electrical air freshener of claim 13 wherein operation of the fan creates air flow into the housing from the inlets at the back of the housing, past the fan, and out through the cartridge.

16. The electrical air freshener of claim 15 wherein the fan comprises a plurality of vanes radiating from a hub.

17. The electrical air freshener of claim 15 wherein the cartridge includes at least on internal spacer sufficient to compartmentalize the pellets into a plurality of compartments within the cartridge.

18. The electrical air freshener of claim 17 wherein the cartridge has a circular cross-section and the at least one spacer comprises two spacers that span perpendicular diameters of the housing, forming four equal compartments.

* * * * *